United States Patent [19]

Pechin et al.

[11] 4,135,821

[45] Jan. 23, 1979

[54] CALIBRATION OF OPTICAL PARTICLE-SIZE ANALYZER

[75] Inventors: William H. Pechin, Oak Ridge; Louis H. Thacker, Knoxville; Lloyd J. Turner, Oak Ridge, all of Tenn.

[73] Assignee: The United States of America as represented by the United States Department of Energy, Washington, D.C.

[21] Appl. No.: 780,159

[22] Filed: Mar. 22, 1977

[51] Int. Cl.² .................................. G01N 15/02
[52] U.S. Cl. .................................. 356/335; 356/243
[58] Field of Search ............... 356/102, 243; 250/252

[56] References Cited

U.S. PATENT DOCUMENTS

| | | | |
|---|---|---|---|
| 2,939,960 | 6/1960 | Gunn | 250/252 |
| 3,614,231 | 10/1971 | Shaw | 356/102 |
| 3,790,760 | 2/1974 | Stiller | 356/102 |

Primary Examiner—Conrad J. Clark
Attorney, Agent, or Firm—Dean E. Carlson; Stephen D. Hamel; Louis M. Deckelmann

[57] ABSTRACT

This invention relates to a system for the calibration of an optical particle-size analyzer of the light-intercepting type for spherical particles, wherein a rotary wheel or disc is provided with radially-extending wires of differing diameters, each wire corresponding to a particular equivalent spherical particle diameter. These wires are passed at an appropriate frequency between the light source and the light detector of the analyzer. The reduction of light as received at the detector is a measure of the size of the wire, and the electronic signal may then be adjusted to provide the desired signal for corresponding spherical particles. This calibrator may be operated at any time without interrupting other processing.

4 Claims, 4 Drawing Figures

CALIBRATION OF OPTICAL PARTICLE-SIZE ANALYZER

BACKGROUND OF THE INVENTION

This invention was made in the course of, or under, a contract with the U.S. Energy Research and Development Administration.

One of the analyses performed on spherical nuclear fuel particles is that of size determination. This is accomplished by singularly passing the particles through a collimated light beam whereby a portion of the light falling upon a detector is intercepted by the particle in proportion to the size. The decrease in light is converted to an individual electrical signal which is then electronically counted and measured. If desired, the signals may be separated according to sizes so that the counting process will provide information as to the number of particles in particular size ranges.

Initially, and periodically thereafter, the calibration of the electronic system must be set and rechecked. One method of calibration is to pass a sample of spherical beads of known sizes repeatedly through the system to obtain sufficient data points (about 200) for adequate statistics. In order to perform this calibration, all regular particles must be removed from the system. The calibration, itself, requires about 30 minutes.

Thus, there exists a need for a more rapid and more convenient means of calibration and/or recalibration of such a system. The present invention was conceived to meet this need in a manner to be described hereinbelow.

SUMMARY OF THE INVENTION

It is the object of the present invention to provide an improved means for the rapid calibration of a particle size analyzer.

The above object has been accomplished in the present invention by repeatedly passing opaque wires of differing but specific sizes between the light source and the detector of the analyzer for a sufficient number of times to achieve statistical accuracy. These wires are mounted on, and project radially from, a rotatable disc which is, in turn, driven by a motor at constant speed. The wire sizes are chosen to calibrate the unit for a specific particle size range.

DESCRIPTION OF THE PREFERRED EMBODIMENT

Figure 1:
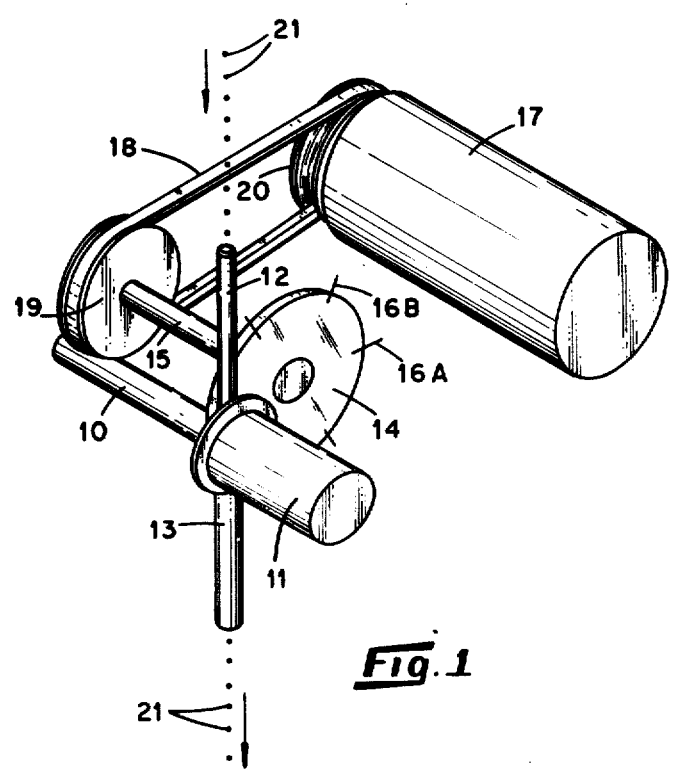
FIG. 1 is a partial isometric view of a particle size analyzer incorporating a calibration means as described hereinbelow.

The calibrator of the present invention is illustrated in FIG. 1 of the drawings, wherein the particle size analyzer itself consists of a collimated light source 10, a detector 11 for measuring transmitted light, and electronic equipment, not shown, for analyzing any decrease in light transmission from the source 10 to the detector 11 to correlate the same with the size of the particle causing the reduced light transmission. The electronic equipment may be, for example, a Nuclear Data Model No. 2400 analyzer. Particles 21 for analysis pass singularly through inlet tube 12, through the light beam from the source 10 and thence through the outlet tube 13 for storage, recycle or other analyses.

A calibrator disc 14, mounted on a shaft 15, is located in near proximity to the path of the light from the source 10. Projecting radially from the disc 14 are a plurality of opaque wires 16A, 16B, etc., each being of a specific but different diameter. The wires 16 may be affixed to the surface of the disc 14 or may be mounted in recesses in the edge of the disc 14. The length of the wires 16 are such that when disc 14 is rotated, the wires will each sweep across the path of the light beam and reduce light transmission to the detector 11. The disc 14 and shaft 15 are typically driven by a motor 17 via a belt 18, a pulley 20, and a pulley 19. It should be understood that during the calibration procedure, no particles 21 are flowing through the inlet tube 12.

In a particular embodiment, the disc 14 was fabricated from sheet plastic and was about 1 ¼ inches in diameter. The disc was rotated at 6180 rpm, for example. In any application the speed of rotation is chosen so that the parameters of the electrical signal derived from the light detector are equivalent to signals derived from the detector when actual particles pass through the analyzer. The principal parameters are the rise time and duration of the pulse so that meaningful comparisons may be made. The high rotational speed (6180 rpm) chosen in this particular application results from the use of vacuum to draw the particles through the analyzer. Obviously, if particles fall through an analyzer only under the effect of gravity, the rise time of resultant signals is longer and therefore the calibration wheel would be rotated at a slower speed to obtain electrical signals having proper pulse parameters. Six metallic wires projected radially from the rim of disc 14 provide six size standards, as follows, to cover the particle size range 380–1000 μm:

| Wire diameter, in. × $10^{-3}$ | Equivalent Particle size, μm |
|---|---|
| 3.0 | 397.3 |
| 6.3 | 563.8 |
| 15.0 | 875.0 |
| 5.0 | 504.1 |
| 10.0 | 717.0 |
| 20.0 | 1005.3 |

Figure 2:
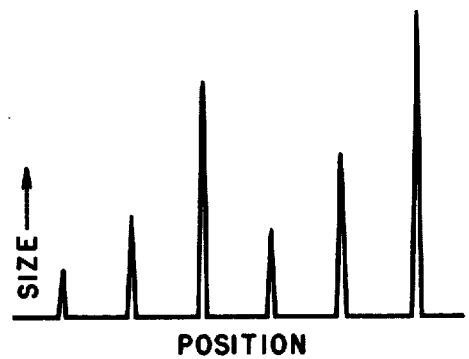
FIG. 2 is an illustration simulating an oscilloscope trace of the light detector output as obtained using the present calibration device.

Referring now to FIG. 2, this is a typical trace from the light detector seen on an oscilloscope when the calibration disc is rotated. It may be seen that the peak heights are proportional to the above-cited wire sizes (equivalent particle sizes) in the order of their passage through the light beam. In this manner the electronic components may be adjusted so that correct sizes may be assigned to acutal particles passing through the analyzer. At the above-cited speed of rotation, about 700 individual measurements of each wire will be made in about 5–7 seconds.

Figure 3:
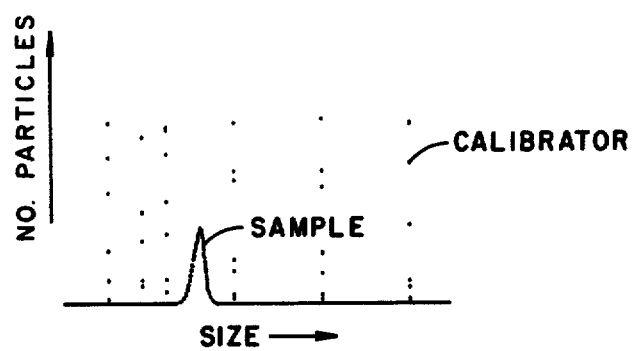
FIG. 3 is an illustration simulating an oscilloscope trace depicting data from the calibration device and an actual sample of particles passing through the particle size analyzer.

FIG. 3 shows a simulation of an oscilloscope trace from the particle size analyzer wherein the calibrator data and data of an actual sample are compared. In this FIGURE, the size is plotted left-to-right (smallest at left), and the total number of a particular size is accumulated in a vertical direction. This illustration shows that the particles within the sample were between 563.8 and 717 μm.

Figure 4:
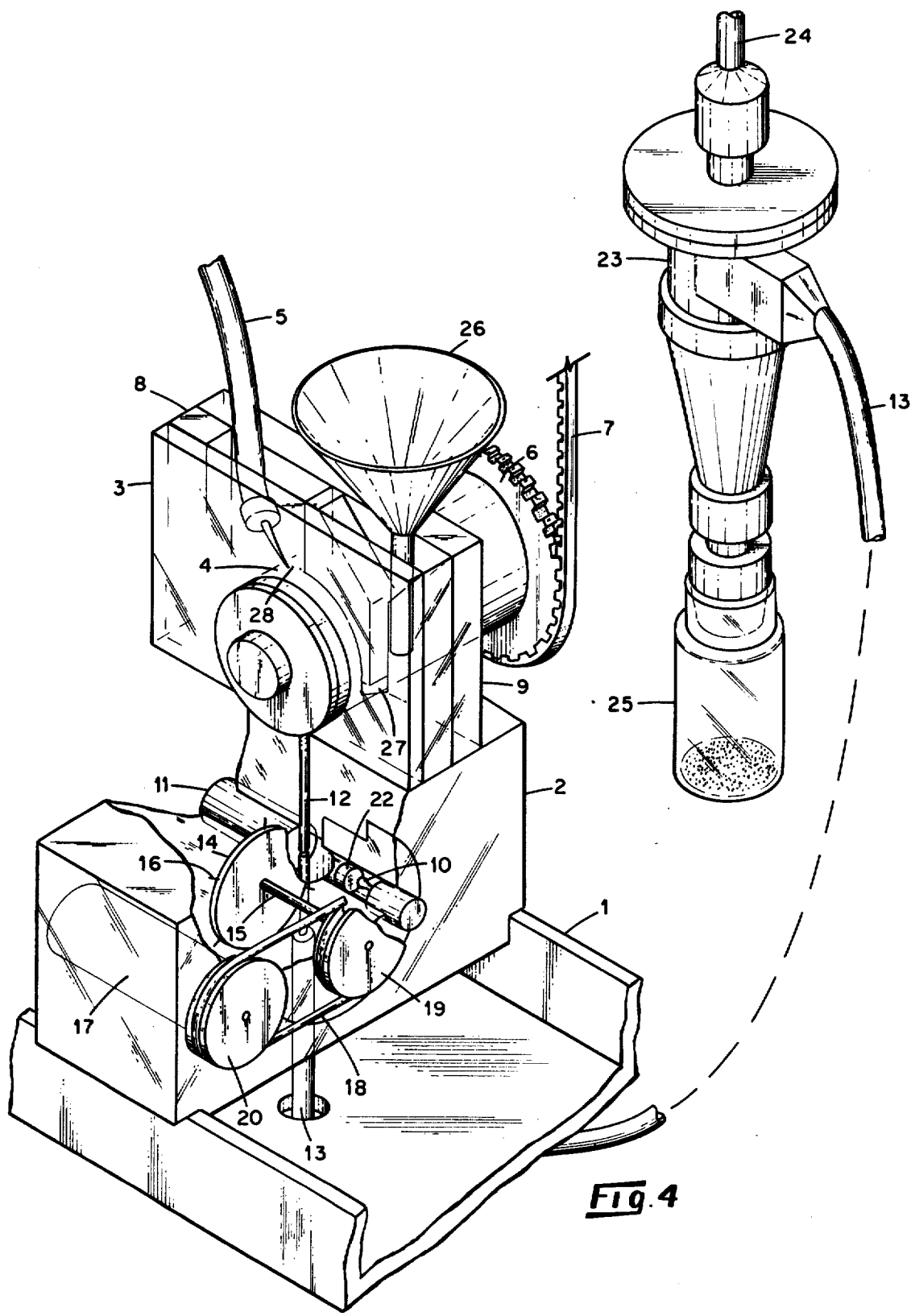
FIG. 4 is an isometric view of that portion of a particle handling system associated with particle size determination and the calibration equipment therefor.

FIG. 4 illustrates the calibrator of FIG. 1 in conjunction with a typical apparatus for feeding particles singularly into the analyzer. It should be noted that the orientation of the components of FIG. 1 are shown displaced 180° from the position of these same components as shown in FIG. 4, for the sake of clarity.

In FIG. 4, a housing 2 is mounted on a U-shaped base member 1. Within the housing 2 is mounted the motor 17 with its pulley 20 extending exterior of the housing 2. The pulley 19 and the drive belt 18 between the pulleys 19 and 20 are also positioned exterior of the housing 2. The calibrator disc 14 and its drive shaft 15 (coupled to the pulley 19) extend to within the housing 2 in a suitable recess provided therefor, and the shaft 15 is supported by any conventional bearing means, not shown.

The particle inlet tube 12 extends downward through the housing 2 in opposing spaced relation to the particle outlet tube 13 which extends upward through the housing to define an air gap therebetween. The light source 10 has its light beam collimated by a suitable lens 22, which collimated beam passes through the air gap between tubes 12 and 13 onto the detector 11, such that each time a particle passes through said gap, the intensity of the light beam reaching the detector 11 is reduced in an amount proportional to the size of the particle.

The disc 14 with its radially extending wires 16, each of different diameters as discussed above, is positioned to one side of the tubes 12 and 13 in such a manner that during a calibration procedure as discussed above, the wires 16 sequentially pass between the collimated light beam from source 10 to the detector 11 to provide the calibration data.

Mounted on top of the housing 2 is an assembly consisting of three rectangular plates 3, 8, and 9, for example, through which an evacuated hollow, rotatable drum 4 extends. This may be, alternatively, a one-piece unit. The drum 4 is provided at one end thereof with a notched driving member 6 which is coupled to a drive belt 7 which in turn, is coupled to a suitable drive motor, not shown. The middle plate 8 is provided with a particle receiving hopper 27 as shown in dashed lines and a particle receiving funnel 26 has its lower portion extending into said hopper as shown in the drawing.

In the rotary drum 4 there are provided a plurality of small holes or apertures 28 arranged in a straight line around the periphery of the drum with the holes sequentially passing over the entrance of the particle inlet feed tube 12. Since the interior of the drum 4 is maintained under a vacuum during the operation of the analyzer, each of the above holes will attract by virtue of said vacuum, a particle from the feed hopper 27 and the single particle will be held thereby. There is provided a jet, not shown, within the drum 4, so positioned with respect to said line of holes and the feed tube 12 that as each hole 28 comes into alignment with the entrance to the tube 12, the jet effects the release of the vacuum-held particle into the tube 12. Furthermore, a vacuum in tubes 12 and 13 draws the released particles through the particle size analyzer. As the drum continues to rotate, another particle from the hopper 27 will then take the place of the just released particle. In the event that two particles are held by any of said holes 28, there is provided a blow-off jet 5 as shown in the drawing for removing the excess particle from the hole.

After the particles have been analyzed by the above-described device, they may be fed by means of the outlet tube 13 to a cyclone separator 23 which is provided with a vacuum line 24 for its operation. The particles fall into a collection bottle or jar 25, for storage, recycle or other analyses.

It will be recognized that the components shown in FIG. 4 may be mounted by means different than those shown therein. Also, other means may be used for sequentially feeding particles into the particle size analyzer.

It should be understood that, if desired, the cyclone separator may be mounted above the funnel 26 with the jar 25 removed and replaced by a suitable vacuum lock (not shown), and thus the same particles may be recycled through the analyzer any desired number of times. In such an operation, it should be evident that standard sized particles could be utilized in the recycling operation to provide primary calibration to the desired statistical accuracy. However, the use of the calibrator disc 14 with its radial wires 16 is the preferred method of subsequent calibration of the analyzer since such calibration is 25 times, or greater, faster than with actual standard size particles and calibration can be performed without altering equipment.

This invention has been described by way of illustration rather than by limitation and it should be evident that it is equally applicable in fields other than those described.

What is claimed is:

1. In an optical particle size analyzer of the type including a source of a collimated light beam, a light detector for receiving said light beam and providing an electrical output proportional to incident light, means for sequentially feeding spherical particles through the path of said light beam whereby a portion of the light beam falling upon said detector is intercepted by each passing particle in proportion to its size, and a read-out circuit coupled to the electrical output of said detector for providing a measure of particle size as well as a count of the number of respective particles measured, the improvement comprising:

a calibration rotary disc provided with a plurality of respective radially extending opaque wires of different diameters, each wire corresponding to a particular equivalent spherical particle diameter; and means for rotating said disc such that each of said wires is passed at a desired frequency between said light beam and said detector, whereby said detector output may be adjusted to provide the desired signal for comparison with corresponding spherical particles when they are subsequently being analyzed by said analyzer.

2. The analyzer set forth in claim 1, wherein said disc is adapted to be rotated at a speed sufficient to produce electrical output signals from the detector having parameters equivalent to signals derived from the detector from particles passing through the analyzer.

3. The analyzer set forth in claim 2, wherein the number of said radially extending disc wires is six in a range of about 3 to 20 μm and thereby provide six size standards in the particle size range from 380–1000 μm.

4. A method of calibrating a light-intercepting analyzer and for determining the, respective sizes of a plurality of spherical particles of different sizes comprising the steps of sequentially and periodically passing a plurality of wires of different diameter between a light source and a light detector of said analyzer, each wire corresponding to a particular spherical particle diameter, to provide a statistical average of the respective output signals of said detector obtained by said passing of said wires between said light source and said detector, adjusting the output of said detector to provide the desired signals for corresponding spherical particles to be analyzed, terminating the passing of said wires, and then passing a plurality of sample particles through said analyzer between said light source and detector to provide a plurality of respective output signals as a function of the respective sizes of said sample particles being analyzed, and comparing the outputs of said detector obtained by the passing of said wires with the outputs of said detector obtained by the passing of said sample particles through said analyzer to provide respective indications of the total number of particles of each respective size.

* * * * *